United States Patent
Plumptre et al.

(10) Patent No.: US 10,099,014 B2
(45) Date of Patent: Oct. 16, 2018

(54) ASSEMBLY FOR A DRUG DELIVERY DEVICE AND DRUG DELIVERY DEVICE WITH SUCH AN ASSEMBLY

(71) Applicant: SANOFI-AVENTIS DEUTSCHLAND GMBH, Frankfurt am Main (DE)

(72) Inventors: David Aubrey Plumptre, Worcestershire (GB); Paul Richard Draper, Worcestershire (GB); David Richard Mercer, Dorset (GB); Naceur Rekaya, Warwickshire (GB); Paul Griffin, Worcestershire (GB)

(73) Assignee: Sanofi-Aventis Deutschland GMBH, Frankfurt am Main ( * ) Notice: Subject to any disclaimer, the term of this patent is extended or adjusted under 35 U.S.C. 154(b) by 356 days.

(21) Appl. No.: 14/770,847

(22) PCT Filed: Mar. 10, 2014

(86) PCT No.: PCT/EP2014/054529
§ 371 (c)(1),
(2) Date: Aug. 27, 2015

(87) PCT Pub. No.: WO2014/139917
PCT Pub. Date: Sep. 18, 2014

(65) Prior Publication Data
US 2016/0008547 A1   Jan. 14, 2016

(30) Foreign Application Priority Data
Mar. 13, 2013 (EP) ..................................... 13159052

(51) Int. Cl.
*A61M 5/31* (2006.01)
*A61M 5/315* (2006.01)

(52) U.S. Cl.
CPC ........ *A61M 5/3146* (2013.01); *A61M 5/3158* (2013.01); *A61M 5/31551* (2013.01);
(Continued)

(58) Field of Classification Search
CPC ............ A61M 5/3146; A61M 5/31538; A61M 5/31551; A61M 5/3158
See application file for complete search history.

(56) References Cited

U.S. PATENT DOCUMENTS

| 533,575 A | 2/1895 | Wilkens |
| 5,226,895 A | 7/1993 | Harris |

(Continued)

FOREIGN PATENT DOCUMENTS

| EP | 0937471 | 8/1999 |
| EP | 0937476 | 8/1999 |

(Continued)

OTHER PUBLICATIONS

Chinese Search Report for CN Application No. 2014800136495, dated Jul. 4, 2017.
(Continued)

*Primary Examiner* — Kevin C Sirmons
*Assistant Examiner* — William Carpenter
(74) *Attorney, Agent, or Firm* — Fish & Richardson P.C.

(57) ABSTRACT

The present disclosure pertains to an assembly for a drug delivery device having a housing part, a piston rod displaceable relative to the housing part, a first sleeve member and a second sleeve member. First and second sleeve members are coupled to the housing part. In an initial state of the assembly the first sleeve member is movable from an initial position to a second position relative to the second sleeve member which allows the piston rod to axially travel from an initial position to a predetermined second position such that the assembly is in a primed state. Moreover, in the
(Continued)

primed state of the assembly, with the first sleeve member being in the second position relative to the second sleeve member, first and second sleeve members are permanently rotationally and axially locked to each other by a first engagement feature such that first and second sleeve members together form a sleeve.

14 Claims, 8 Drawing Sheets

(52) U.S. Cl.
CPC ............... *A61M 2005/3126* (2013.01); *A61M 2205/6018* (2013.01)

(56) References Cited

U.S. PATENT DOCUMENTS

| | | | |
|---|---|---|---|
| 5,279,586 | A | 1/1994 | Balkwill |
| 5,304,152 | A | 4/1994 | Sams |
| 5,320,609 | A | 6/1994 | Haber et al. |
| 5,383,865 | A | 1/1995 | Michel |
| 5,480,387 | A | 1/1996 | Gabriel et al. |
| 5,505,704 | A | 4/1996 | Pawelka et al. |
| 5,582,598 | A | 12/1996 | Chanoch |
| 5,626,566 | A | 5/1997 | Petersen et al. |
| 5,674,204 | A | 10/1997 | Chanoch |
| 5,688,251 | A | 11/1997 | Chanoch |
| 5,921,966 | A | 7/1999 | Bendek et al. |
| 5,961,495 | A | 10/1999 | Walters et al. |
| 6,004,297 | A | 12/1999 | Steenfeldt-Jensen et al. |
| 6,193,698 | B1 | 2/2001 | Kirchhofer et al. |
| 6,221,046 | B1 | 4/2001 | Burroughs et al. |
| 6,235,004 | B1 | 5/2001 | Steenfeldt-Jensen et al. |
| 6,248,095 | B1 | 6/2001 | Giambattista et al. |
| 6,899,698 | B2 | 5/2005 | Sams |
| 6,936,032 | B1 | 8/2005 | Bush, Jr. et al. |
| 7,241,278 | B2 | 7/2007 | Moller |
| 2002/0052578 | A1 | 5/2002 | Moller |
| 2002/0120235 | A1 | 8/2002 | Enggaard |
| 2003/0050609 | A1 | 3/2003 | Sams |
| 2004/0059299 | A1 | 3/2004 | Moller |
| 2004/0210199 | A1 | 10/2004 | Atterbury et al. |
| 2004/0267207 | A1 | 12/2004 | Veasey et al. |
| 2005/0113765 | A1 | 5/2005 | Veasey et al. |
| 2005/0261634 | A1* | 11/2005 | Karlsson ............... A61M 5/20 604/197 |
| 2006/0153693 | A1 | 7/2006 | Fiechter et al. |
| 2009/0275916 | A1 | 11/2009 | Harms et al. |
| 2010/0331789 | A1* | 12/2010 | Jones ..................... A61M 5/24 604/207 |
| 2012/0289908 | A1* | 11/2012 | Kouyoumjian ... A61M 5/31543 604/211 |

FOREIGN PATENT DOCUMENTS

| | | |
|---|---|---|
| JP | 2012-528620 A | 11/2012 |
| JP | 2012-528627 A | 11/2012 |
| WO | 99/38554 | 8/1999 |
| WO | 01/10484 | 2/2001 |
| WO | 2010/139631 A1 | 12/2010 |
| WO | 2010/139639 A1 | 12/2010 |
| WO | 2011/039229 | 4/2011 |
| WO | 2011/039236 | 4/2011 |
| WO | 2011/039239 | 4/2011 |
| WO | 2011/042538 | 4/2011 |

OTHER PUBLICATIONS

International Search Report for Int. App. No. PCT/EP2014/054529, completed Jul. 8, 2014.
Japanese Office Action for JP Application No. 2015-562059, dated Dec. 19, 2017.

* cited by examiner

ASSEMBLY FOR A DRUG DELIVERY DEVICE AND DRUG DELIVERY DEVICE WITH SUCH AN ASSEMBLY

CROSS REFERENCE TO RELATED APPLICATIONS

The present application is a U.S. National Phase Application pursuant to 35 U.S.C. § 371 of International Application No. PCT/EP2014/054529 filed Mar. 10, 2014, which claims priority to European Patent Application No. 13159052.3 filed Mar. 13, 2013. The entire disclosure contents of these applications are herewith incorporated by reference into the present application.

TECHNICAL FIELD

The present disclosure is generally directed to an assembly for a drug delivery device and a respective drug delivery device comprising such an assembly.

BACKGROUND

Drug delivery devices have become widespread in the field of medical treatment where regular injection of a medicament by persons without formal medical training occurs. For example, this may be increasingly common among patients having diabetes where self-treatment enables such patients to conduct effective management of their disease.

There are different types of drug delivery devices. On the one hand, one can differentiate between resettable devices which are reusable and non-resettable devices which are disposable. For example, the disposable delivery devices are supplied as self-contained devices. Such self-contained devices do not have removable pre-filled cartridges. Rather, the pre-filled cartridges may not be removed and replaced from these devices without destroying the device itself.

On the other hand, one can differentiate between so-called fixed dose devices which only allow dispensing of a predefined dose without the possibility to increase or decrease the set dose and so-called variable dose devices which allow a user to individually select and dispense a number of user variable doses of a medicament. In general, all these types of delivery devices can be pen-shaped.

The drug delivery devices as explained above generally comprise several primary elements, for example a cartridge section that includes a cartridge which can be contained within a housing or holder, a needle assembly connected to one end of the cartridge section, and an additional assembly which may enable dialing and/or delivery of a dose of a medicament. The latter assembly can be connected to the end of the cartridge section which is located away from the needle assembly. A cartridge (often referred to as an ampoule) typically includes a reservoir that is filled with a medication (for example insulin), a movable bung or piston or stopper located at one end of the cartridge reservoir, and a top having a pierceable seal or sheath located at the other, often necked-down end.

The assembly for dialing and/or delivering a dose of a medicament may comprise a housing part and a piston rod or lead screw which is displaceable relative to the housing part. The piston rod is designed to push the bung or stopper of the cartridge in a direction to an outlet of the cartridge such that the medication can be expelled out of the device and delivered to a patient. In an initial state, for example a supplied state of the device, there can be a certain gap or clearance between the end of the piston rod and the bung of the cartridge when these parts are assembled. For example, the mentioned gap can be a consequence of tolerances associated with all or many of the assembled parts and/or the desire not to pre-load the bung of the cartridge in the assembled state of the device. The latter fact would have the consequence that medication might be unintentionally expelled out of the device.

A gap between the end of the piston rod and the cartridge bung can have several disadvantages. One disadvantage may arise if a user takes the device for the first time for an intended injection of a predetermined dose of a medicament. The actual dose received will then be equal to the predetermined dose less the initial air gap between the piston rod and the bung. For example, this air gap is typically equivalent to a loss of between 0 and 0.14 ml on the first dose. For many drugs, this discrepancy can be significant and is well outside the allowable dose accuracy limits. At present, it is conventional use, therefore, for the user to be instructed to perform a so-called "air shot" which means that the user has to operate the device for the first time without injecting the medication into his body but in the air until the gap between the piston rod and the bung is traversed and fluid may begin to be ejected.

This course of action has the additional disadvantage that expensive medication potentially has to be discarded before the user may take the first injection of the medicament. This may result in rising costs for the medication and/or the drug delivery device.

It is, therefore, an object to describe an assembly for a drug delivery device as well as a drug delivery device with such an assembly which are designed so that the gap between the piston rod and the cartridge bung can be removed (transition from an initial state to a primed state) before a first dose of a medicament is injected.

SUMMARY

In a first aspect, this object is solved by an assembly for a drug delivery device according to claim 1. The assembly comprises a housing part, a piston rod displaceable relative to the housing part, a first sleeve member and a second sleeve member, first and second sleeve members being coupled to the housing part. In an initial state of the assembly, the first sleeve member is movable from an initial position to a second position relative to the second sleeve member which allows the piston rod to axially travel from an initial position to a predetermined second position such that the assembly is in a primed state. In the primed state of the assembly, with the first sleeve member being in the second position relative to the second sleeve member, first and second sleeve members are permanently rotationally and axially locked to each other by a first engagement feature such that first and second sleeve members together form a sleeve.

The assembly provides features for a transition from an initial state, which may be a delivered state or delivered condition of the assembly, to a primed state in which the assembly is ready for a first dose of a medicament within a drug delivery device to be ejected out of the device. During the transition from the initial state to the primed state, the piston rod is enabled to axially travel with respect to the housing part of the assembly from an initial position to a predetermined second position. That means, in the initial state of the assembly the piston rod is enabled to axially travel with respect to the housing such that a gap or clearance between the piston rod and a cartridge bung of a drug delivery device, with the assembly assembled into the drug delivery device, can be removed or traversed. The axial travel or movement of the piston rod from its initial position to its predetermined second position (i.e. the transition from the initial state to the primed state of the assembly) is enabled by the first sleeve member being movable from a respective initial position to a respective second position relative to the second sleeve member of the assembly. That means, the movement of the first sleeve member relative to the second sleeve member in the initial state of the assembly is related to the axial travel of the piston rod from its initial position to its predetermined second position.

In the primed state of the assembly, the first and second sleeve members are permanently rotationally and axially locked to each other by a first engagement feature, wherein first and second sleeve members together form a single sleeve. In the primed state, the first sleeve member is brought in its second position relative to the second sleeve member. That means, upon movement of the first sleeve member from its initial position to its second position relative to the second sleeve member, the further interaction of first and second sleeve members with other parts of the assembly takes place in such a way that first and second sleeve members can only be moved together and, therefore, have a functional behavior of one single piece with regard to other parts of the assembly.

Since in the primed state of the assembly a movement of the first sleeve member relative to the second sleeve member is prevented (due to their permanently rotationally and axially locking interaction), a further movement of the piston rod as during the transition from the initial state to the primed state of the assembly is prevented, too. That means, a transition of the piston rod from the initial state to the primed state, i.e. an axial travel of the piston rod in order to perform this transition, is only enabled as long as the first sleeve member is movable relative to the second sleeve member. Once the first sleeve member has taken its second position relative to the second sleeve member, the assembly is in its primed state, wherein a further axial travel of the piston rod in order to perform the transition into the primed state is no longer possible.

The term "primed state" in this context shall be understood as a state of the assembly in which the assembly is in a ready-to-use-state; that means the assembly can be further operated by a user for dialing and/or delivering a predetermined amount of a medicament when assembled into a drug delivery device. As such, the primed state provides a state in which "normal" operation of the assembly can be performed.

An initial movement of the first sleeve member relative to the second sleeve member can be designed such that an axial travel of the piston rod is delimited to a predetermined distance corresponding to an air gap between the end of the piston rod and a cartridge bung of a drug delivery device in which the assembly can be used. The measures as explained above have the advantage that the air gap can be traversed without the user being expected to perform "air shots" discarding medication for preparing a drug delivery device for the first injection. The explained assembly provides features allowing a user to perform a priming action in order to transfer the assembly from its initial state into its primed state, i.e. to remove an air gap between the end of the piston rod and the cartridge bung, in a convenient and simple way such that a drug delivery device in which the assembly is used can be prepared for the first use in a better way than is the case in conventional known solutions.

According to a first embodiment of the assembly, the functional relationship between the first and/or the second sleeve member and the piston rod can be designed such that a movement of the first sleeve member relative to the second sleeve member only enables an axial movement of the piston rod. That means, the axial travel of the piston rod is not generated by a movement of the first sleeve member relative to the second sleeve member, but is delimited and therefore in a sense controlled by the movement of the first sleeve member relative to the second sleeve member. An axial travel of the piston rod in this case is only allowed as long as the first sleeve member is in fact movable relative to the second sleeve member. When the first sleeve member is in a second position relative to the second sleeve member, no further axial travel of the piston rod for priming the assembly is possible.

In this embodiment, an axial movement of the piston rod can, for example, be generated by a user pushing the piston rod directly or indirectly via another coupling member in axial direction relative to the housing part of the assembly.

According to an alternative second embodiment, the movement of the first sleeve member relative to the second sleeve member not only controls or delimits an axial travel of the piston rod, but also generates such a movement of the piston rod. In this case, first and second sleeve members may act as direct or indirect driving members for driving the piston rod. In this context, it is conceivable that a user operates the first sleeve member and moves it relative to the second sleeve member such that the piston rod (directly or indirectly coupled to the first and/or second sleeve member) can axially travel from its initial position to its second position, i.e. into the primed state of the assembly.

An important fact of all of the mentioned embodiments is that an axial movement of the piston rod for traversing the assembly from its initial state into its primed state can only be performed with the first sleeve member being movable relative to the second sleeve member. In the primed state of the assembly, the first sleeve member is in its second position relative to the second sleeve member and is rotationally and axially locked to the second sleeve member and, therefore, cannot further move relative to the second sleeve member. In this state, the assembly is fully primed, such that no further axial travel of the piston rod in order to perform the transition into the primed state is necessary or allowed.

Certainly, the explained features do not prevent any further movement of the piston rod during the further use of the assembly. That would be against the intention of the assembly for dialing and/or delivering a dose of a medicament as used in a drug delivery device. It is essential that any further operation of the assembly and any movement of the piston rod relating therefrom are caused by means of features of the assembly, with first and second sleeve members together acting as one piece or sleeve, respectively. The functionality of first and second sleeve members as to enable the piston rod to axially move into a primed state as explained above is completed during further operation of the assembly.

In one embodiment, the assembly may comprise a driver coupled to the piston rod for driving the piston rod. That means any movement of the piston rod (or only a selected movement of the piston rod) can be driven by the driver. Hence, the driver may act as a coupling member between a user's operational action and a movement of the piston rod resulting therefrom. In this aspect, the driver transmits an operational action into a movement of the piston rod.

Alternatively or in combination with this embodiment, the assembly may comprise a button which may be arranged at a proximal end of the assembly and which may be coupled to the first sleeve member. In the case that the assembly provides a driver as explained above, the button may also be coupled to the driver. The button may provide another coupling feature, besides a potential driver, for coupling a user's operational action with the movement of either or both of the first sleeve member and the piston rod.

The term "proximal end" in this context means an end of the assembly which is in greater distance from a needle part of a drug delivery device in which the assembly is used than the other end of the assembly. This can mean for a drug delivery device, especially a pen-shaped device, with such an assembly that one end of the drug delivery device forms a needle assembly of a cartridge holder and the other end of the drug delivery device is formed by the proximal end of the assembly as explained above. Briefly, the proximal end of the assembly is the end the most distant from a body site of a patient when operating a drug delivery device for injection of a medicament into the body.

In the initial state of the assembly, the button is preferably enabled to axially travel relative to the second sleeve member, the button during its axial travel entraining the driver such that the driver is axially displaced relative to the housing part, thereby urging the piston rod into its axial movement from the initial position to the predetermined second position in order to bring the assembly into its primed state. In this embodiment, the button may be coupled to the first sleeve member and to the driver, wherein the driver per se is coupled to the piston rod. Accordingly, an axial movement of the button relative to the second sleeve member is enabled by the first sleeve member being movable relative to the second sleeve member correspondingly.

The first sleeve member can, for example, be axially movable and/or rotatable with respect to the second sleeve member. During its axial travel, the button entrains the driver such that the driver is axially displaced relative to the housing part. The driver in turn urges the piston rod into its axial movement from the initial position to the primed position. This movement of the discrete parts button, driver, and piston rod is enabled until the first sleeve member is in its second position relative to the second sleeve member. Once the first sleeve member has taken the latter position, a further axial travel of the button causing a transition of the piston rod from its initial position to its primed position is no longer possible. In this embodiment, a user may, for example, be instructed to press the button which is arranged at the proximal end of the assembly for priming the assembly in order to prepare a drug delivery device in which the assembly is used for the first injection.

According to one embodiment, the first sleeve member engages with the second sleeve member via a second engagement feature such that in the initial position of the first sleeve member, a maximum clearance between respective walls of first and second sleeve members is limited to a predetermined clearance. That means a movement of the first sleeve member relative to the second sleeve member can be delimited via the second engagement feature. Hence, movement of the first sleeve member relative to the second sleeve member is controlled and delimited by a predetermined path and/or distance between respective walls and/or parts of first and second sleeve members. For example, a movement of the first sleeve member is only admissible in order to traverse an initial clearance between first and second sleeve members, wherein the first sleeve member can be moved towards the second sleeve member, but not in a direction away from the second sleeve member. This feature may have the advantage that according to an embodiment, wherein a user may operate a button for priming the assembly can only press the button into a housing of the assembly but cannot pull the button out of the housing of the assembly. Hence, this feature provides an easy-to-use function enabling an improved handling of the assembly, especially for users with limited dexterity.

According to one preferable embodiment, the movement of the first sleeve member from its initial position to its second position relative to the second sleeve member is non-reversible. Once the first sleeve member has moved from its initial position to its second position relative to a second sleeve member and has consequently taken the second position, a reverse movement of the first sleeve member back from the second position in a direction towards the first position is prevented. This feature can be supported by the first engagement feature as explained above by which first and second sleeve members are permanently rotationally and axially locked to each other in the second position of the first sleeve member relative to the second sleeve member. The non-reversible feature as explained in this context has the advantage that, once the assembly has been traversed from its initial state to its primed state, the assembly remains in the primed state during further operation of the assembly. A subsequent manipulation of the first sleeve member for moving the first sleeve member relative to the second sleeve member is prevented in the primed state. Accordingly, the assembly takes a secure state after the transition from the initial state to the primed state has been performed. Another advantage of the non-reversible feature is that a user may be enabled to easily spot whether the assembly is still in its initial state or already in its primed state.

According to one embodiment, the first sleeve member engages with the housing part via a third engagement feature such that between the initial position and the second position of the first sleeve member relative to the second sleeve member, a rotational movement of the first sleeve member relative to the housing part is prevented. This feature delimits a movement of the first sleeve member to an axial movement with respect to the housing part during a transition from the initial state to a primed state of the assembly. In an exemplary embodiment, the first sleeve member in combination with either or both of a driver or a button can only be axially moved with respect to the housing part, wherein the driver and/or button are axially moved with respect to the housing part, too.

Hence, the assembly can be designed such that a user presses the button in an axial direction, wherein the first sleeve member (potentially in combination with the driver) is also axially moved with respect to the housing. Accordingly, the piston rod travels axially into the primed state as explained above. During this movement, a rotational movement of either or both of the button and the first sleeve member is prevented by the above-explained feature. This has the advantage that, for example, any rotational dialing action (if such an action is permitted by the design and use of the assembly in combination with a respective drug delivery device) is prevented as long as a transition of the assembly from the initial state to the primed state has not been fully performed, and is firstly enabled, when the assembly has taken its primed state with the piston rod having traversed the air gap between its end and a cartridge bung of an assembled drug delivery device as explained in the context above. Therefore, such an assembly provides secure and improved handling, especially for a user with limited dexterity, since any operational movement is controlled by the assembly itself. A user cannot perform any wrong operational movement.

According to one embodiment, the second sleeve member comprises an inner thread engaging an outer thread of the housing part such that the second sleeve member is movable on a helical path relative to the housing part. Additionally, first and second sleeve members can be in threaded engagement with each other, wherein the movement of the first sleeve member from its initial position to its second position relative to the second sleeve member urges the second sleeve member into a rotational movement relative to the housing part and to the first sleeve member such that the second sleeve member moves on the helical path relative to the housing part in a direction opposite to the direction of movement of the first sleeve member.

The explained feature enables the second sleeve member to react on a movement of the first sleeve member relative to the second sleeve member such that the movement of the first sleeve member urges the second sleeve member into a respective movement. This coupling is fulfilled by a threaded engagement of first and second sleeve members. For example, the first sleeve member can axially travel with respect to the housing part of the assembly and with respect to the second sleeve member, such that due to the threaded engagement of the two members, the second sleeve member is urged into a rotational movement relative to the housing part and to the first sleeve member. Accordingly, the second sleeve member rotates as long as the first sleeve member moves axially with respect to the housing part and the second sleeve member. By this feature, additional functionality of the assembly can be performed.

In this context, an additional functionality can, for example, be given in such a way that during movement of the second sleeve member relative to the housing part (caused by a movement of the first sleeve member as explained above) a display information provided by the second sleeve member can be designed to change from an initial state information to a primed state information. That means, movement of the second sleeve member can indicate the transition of the assembly from the initial state to the primed state. As such, the movement of the first sleeve member relative to the second sleeve member can fulfill two functionalities. The first functionality is given by the explanations above, wherein a movement of the piston rod from its initial position to its predetermined second position, i.e. the primed state, is enabled as long as the first sleeve member is movable relative to the second sleeve member. The second functionality is given in so far as first and second sleeve members are coupled, wherein a movement of the first sleeve member causes a movement of the second sleeve member, for example in order to indicate that a priming action is or has been performed.

Preferably, the second sleeve member is designed as so-called number sleeve and provides dosing indicia for setting a predetermined dose of a medicament. With the dosing indicia indicating the doses of a medicament, a user can dial a dose by visually controlling the amount of medicament set in the assembly via the dosing indicia of the second sleeve member.

According to another aspect, the above-mentioned object is also solved by a drug delivery device for selecting and dispensing a number of doses of a medicament, comprising a housing, a cartridge containing the medicament and an assembly of the type explained above.

The terms "medicament", "medication" and "drug" as well as mentioned equivalents, as used herein, preferably mean a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(w-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39), des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Preferable and/or alternative embodiments as well as further features of an assembly and of a drug delivery device of the type explained above are disclosed and described in the depending claims as well as with reference to the accompanying drawings, in which:

DETAILED DESCRIPTION

Figure 1:
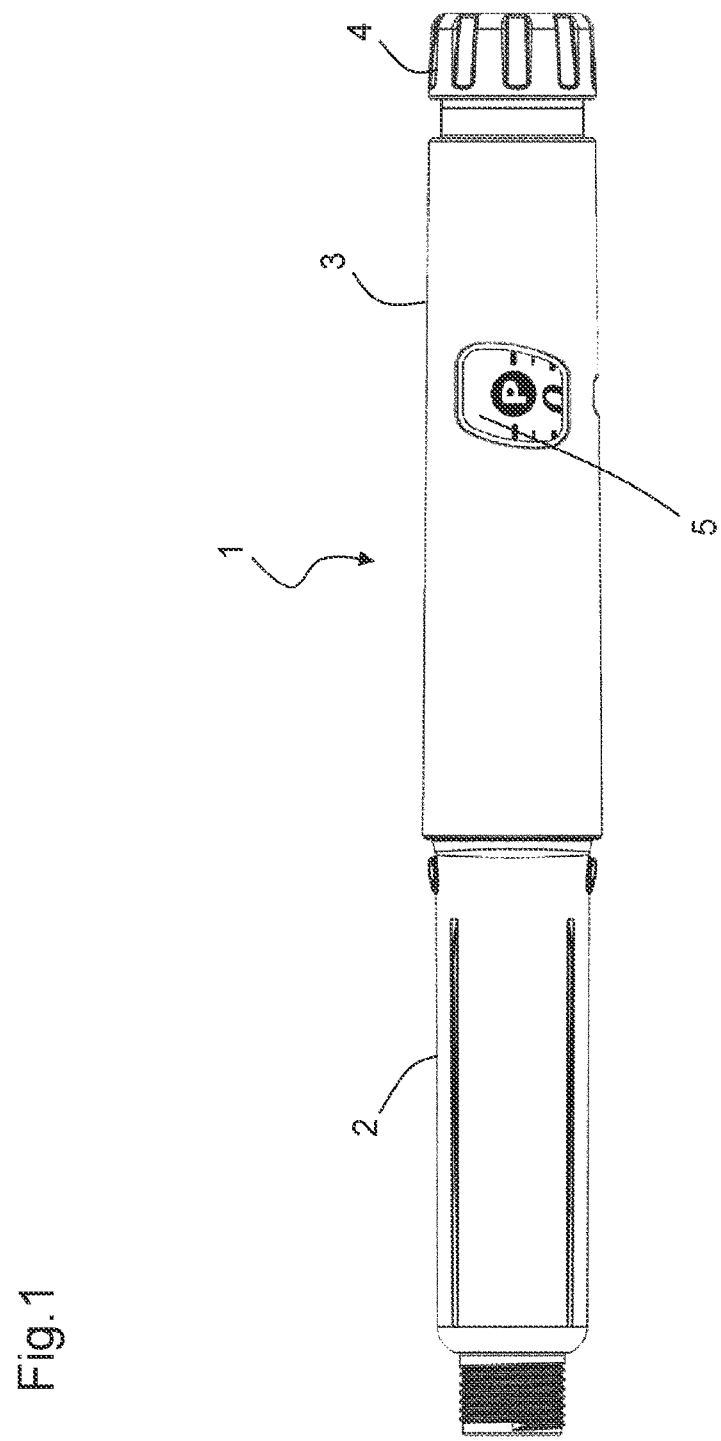
FIG. 1 shows a side view of a drug delivery device in an initial state in accordance with the present disclosure.

FIG. 1 shows a side view of a drug delivery device 1 in an initial state of the drug delivery device 1. The drug delivery device 1 comprises a cartridge 2 and an outer housing 3 which is coupled to the cartridge 2 and accommodates components of an assembly for dialing and/or dispensing medication out of the cartridge 2 for delivery to a patient.

The cartridge 2 may contain a predetermined amount of a medication and provides a thread feature at its left end for mounting a needle assembly (not shown) in order to inject the medication out of the cartridge 2 into a body site of a patient. Moreover, the cartridge 2 provides a bung or stopper (not shown) which is arranged inside the cartridge 2 and which can be pushed towards the left end of the drug delivery device 1, i.e. towards the thread feature for the needle assembly of the cartridge 2, in order to expel the medication out of the cartridge 2 via a predetermined pressure force.

The outer housing 3 accommodates, besides other parts and components which are explained below, a piston rod (not shown) which is designed to be driven by a user's operational action in order to push a bung of the cartridge 2 in the left direction for expelling the medicament out of the device 1. In particular, the piston rod can be driven by components and members as explained below.

Besides a piston rod, the outer housing 3 accommodates other parts and components of which display information 5 (through a translucent window in the outer housing 3) and a button 4 as well as a part of an inner component of the outer housing 3 are shown. The button 4 is arranged at a right end of the drug delivery device 1.

In general, the left end of the device 1 is called "distal end" and is located the nearest to a body site of a patient during intended operation of the drug delivery device 1 for injection of the medicament into the body of the patient. The right end of the device 1 is called "proximal end" and is located the most distant from a body site of a patient.

In the initial state of the device 1 according to FIG. 1, a delivered or supplied state of the device 1 is depicted. That means, the device 1 as shown in FIG. 1 is supplied to a user. In this state, there is an air gap (not shown in FIG. 1, explained in the context of FIG. 8) between the cartridge bung and one end of the piston rod which during intended operation abuts the bung of the cartridge for medication delivery as explained above. The air gap can be a consequence of tolerances associated with all assembled parts of the device 1 and results from the desire not to pre-load the cartridge bung axially in left direction in the assembled device in order to prevent unintended injection of medication out of the device 1.

Figure 2:
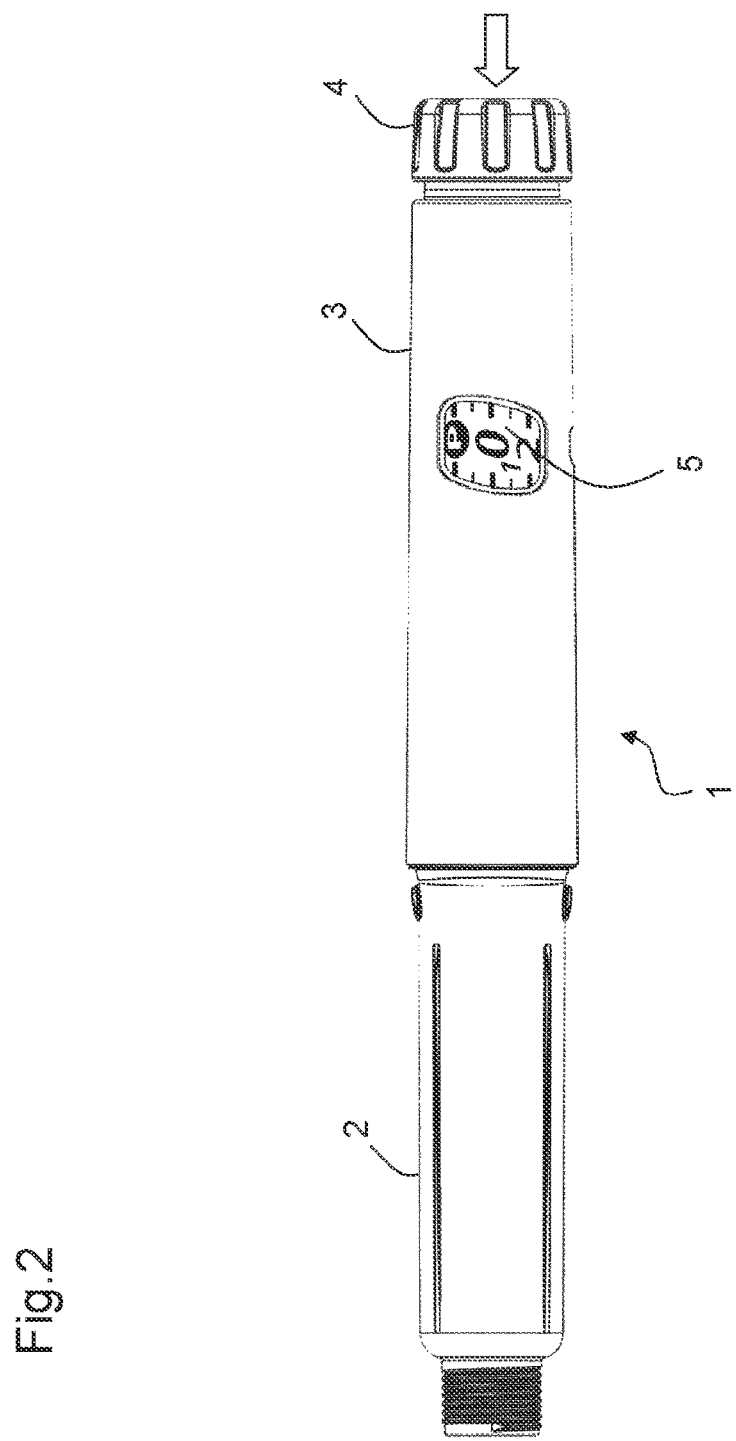
FIG. 2 shows the drug delivery device according to FIG. 1 in a primed state.

The air gap between the piston rod and the bung can be traversed by a transition of the drug delivery device 1 from the initial state as depicted in FIG. 1 to a so-called "primed state" according to FIG. 2, wherein in the primed state the piston rod has been axially moved such that it abuts with one end at the bung of the cartridge 2, a further axial travel of the piston rod effecting an ejection of medicament out of the device 1.

FIG. 2 shows the device 1 according to FIG. 1, but now in the primed state, with the button 4 being pressed in left direction into the outer housing 3 (see the arrow). Consequently, the display information 5 has been changed from a priming indicia according to FIG. 1 into a ready-to-operate indicia (e.g. the number "0" to indicate readiness of the device 1) according to FIG. 2.

According to the embodiment of FIGS. 1 and 2, the axial travel of the button 4 from the initial position according to FIG. 1 into the primed position according to FIG. 2 causes the piston rod within the outer housing 3 of the device 1 to axially travel in left direction, wherein its axial travel is designed such that in the primed position according to FIG. 2, the piston rod abuts the cartridge bung of the cartridge 2, with the device 1 being ready for further operation. Further operation of the device 1 is explained in the context of FIGS. 7 and 8.

Figure 3:
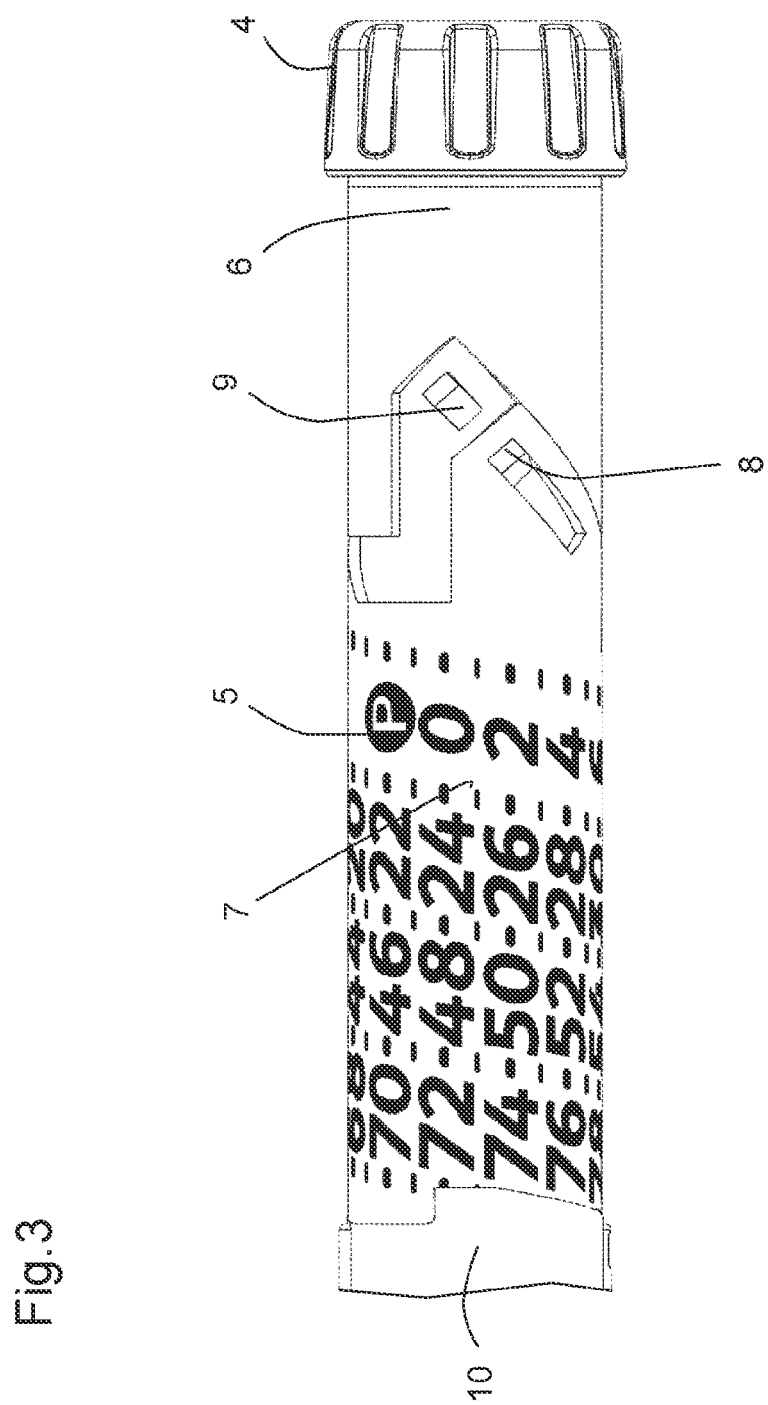
FIG. 3 shows a side view of parts of the drug delivery device according to FIG. 1.
Figure 4:
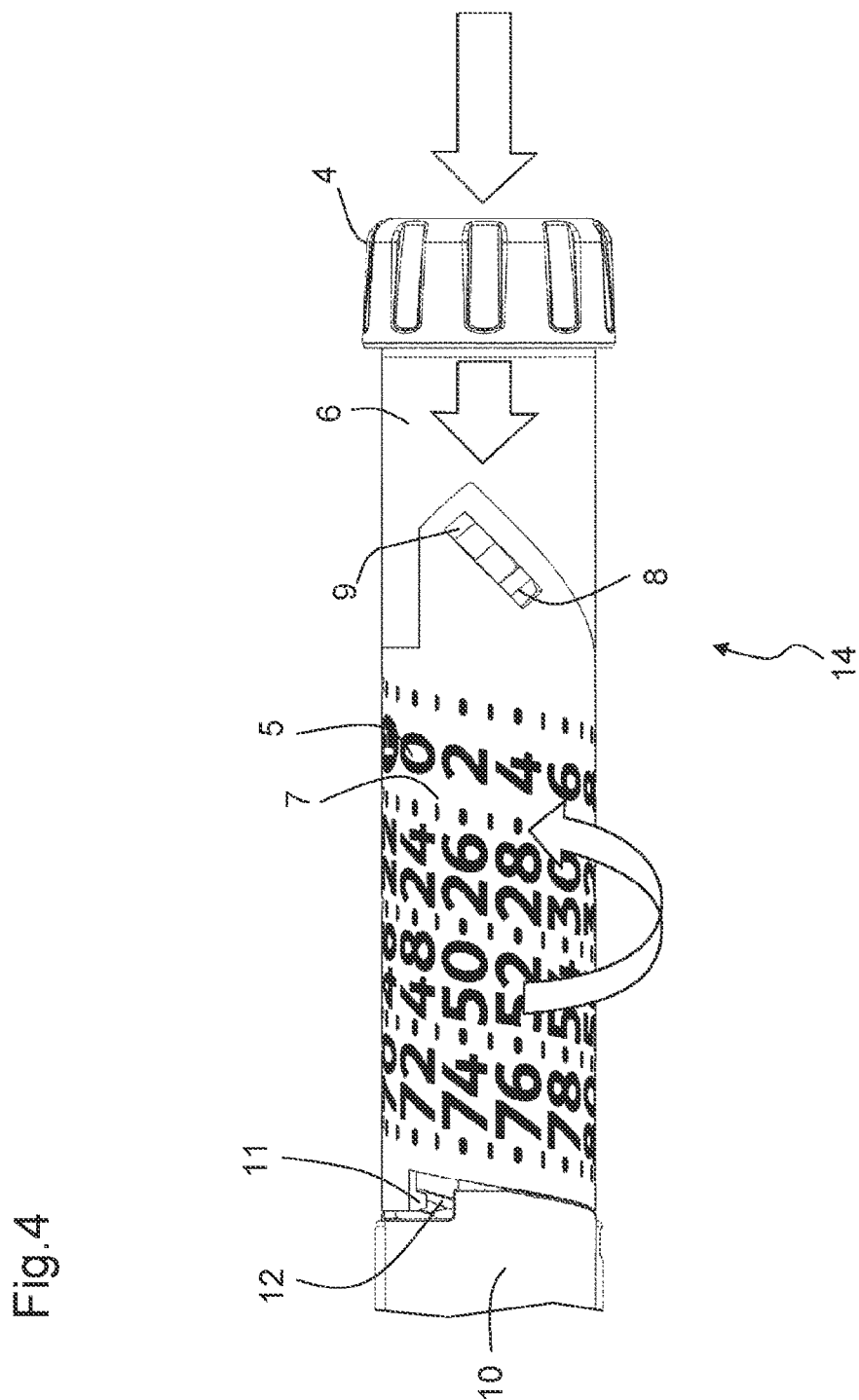
FIG. 4 shows a side view of parts of the drug delivery device according to FIG. 2.

FIGS. 3 and 4 show interior parts and components of the drug delivery device 1 according to FIGS. 1 and 2 which are at least partly accommodated by the outer housing 3 of the device 1. FIG. 3 shows a part of the device in the initial state according to FIG. 1, wherein FIG. 4 shows a part of the device in the primed state according to FIG. 2. In both FIGS. 3 and 4, the outer housing 3 is hidden in order to better illustrate the mechanical interaction of the several components within the device 1.

FIG. 3 depicts a part of an inner housing 10, a first sleeve member 6, a second sleeve member 7 and a button 4 (see also FIGS. 1 and 2). First and second sleeve members 6, 7 are arranged around an outer part of the inner housing 10. The button 4 is coupled to the first sleeve member 6, wherein the first sleeve member 6 is movable with respect to the second sleeve member 7. That means, the first sleeve member 6 can be moved from its initial position with respect to the second sleeve member 7 according to FIG. 3 into a second position with respect to the second sleeve member 7 according to FIG. 4. In particular, by pressing the button 4 in left direction, the first sleeve member 6 can axially travel together with the button 4 in left direction such that a transition of the components from the situation as depicted in FIG. 3 to the situation as depicted in FIG. 4 can be performed.

In detail, an axial travel of the button 4 together with the first sleeve member 6 in left direction urges the second sleeve member 7 into a rotational movement with respect to the inner housing 10 and the first sleeve member 6, since first and second sleeve members 6, 7 are in threaded engagement with each other. According to FIGS. 3 and 4, respective walls of a thread section (i.e. a section with an axial and a circular portion) interact with each other such that an axial movement of the first sleeve member 6 in left direction urges the second sleeve member 7 into a rotational movement.

The first sleeve member 6 provides an engagement feature 8 which interacts with the second sleeve member 7 in order to delimit the maximum axial clearance between first and second sleeve members 6, 7 to an axial clearance as depicted in FIG. 3 (the initial position of the components). That means, the first sleeve member 6 cannot be moved in the right direction away from the second sleeve member 7. This provides a safety feature for preventing that a user pulls the first sleeve member 6 with the button 4 out of the drug delivery device 1 in right direction. Only a movement in left direction of the button 4 together with the first sleeve member 6 is permitted.

FIG. 4 shows the situation, when the button 4 and the first sleeve member 6 have traveled in left direction towards the second sleeve member 7, wherein the second sleeve member 7 has rotated caused by the threaded engagement with the first sleeve member 6. In this way, the second sleeve member 7 has traveled on a helical path with respect to the inner housing 10 due to a threaded engagement of an inner thread 11 of the second sleeve member 7 with an outer thread 12 of the inner housing 10. In this way, display information 5 showing a priming indicia (symbolized with a white P on a colored background) according to FIG. 3 has been changed to a display information 5 (symbolized by the number "0") indicating a ready-to-use state or primed state of the device according to FIG. 4. That means, the priming indicia has rotated in clockwise direction as symbolized by a circular arrow as depicted in FIG. 4.

In the state of FIG. 4, first and second sleeve members 6, 7 are in keyed contact with each other, wherein the first sleeve member 6 now engages with the second sleeve member 7 via another engagement feature 9, besides the first engagement feature 8, such that first and second sleeve members 6, 7 are permanently rotationally and axially locked to each other. That means, first and second sleeve members 6, 7 together form a single piece or sleeve 14. Further operation of the components can only be fulfilled with first and second sleeve members 6, 7 together moving in a consistent way. With the aid of the second engagement feature 9, a relational movement of first and second sleeve members 6, 7 to each other as for a transition between FIGS. 3 and 4 is non-reversible, which means that the first sleeve member 6 cannot be separated anymore from the second sleeve member 7 when the first sleeve member 6 has reached its position according to FIG. 4.

The axial clearance between respective walls of first and second sleeve members 6, 7 according to FIG. 3 enables the first sleeve member 6 to move with respect to the second sleeve member 7 in the left direction. This in turn enables the button 4 to move together with the first sleeve member 6, as explained above, in left direction, such that the transition between FIGS. 3 and 4 can be performed (see axial arrows in FIG. 4). The axial travel of the button 4 and the first sleeve member 6 causes a piston rod (not shown in FIGS. 3 and 4) to axially move in left direction such that the piston rod can be traversed from an initial position to a predetermined second position which provides the primed state of a drug delivery device 1 as explained in the context of FIGS. 1 and 2. When the button 4 and in particular the first sleeve member 6 are in the second position with respect to the second sleeve member 7 as depicted in FIG. 4, a further axial travel of the piston rod during such a movement of the button 4 and the first sleeve member 6 with respect to the second sleeve member 7 is prevented. That means, the situation in FIG. 4 illustrates a secure state of the drug delivery device 1, wherein an air gap between an end of the piston rod and a cartridge bung of the cartridge 2 is removed.

Figure 5:
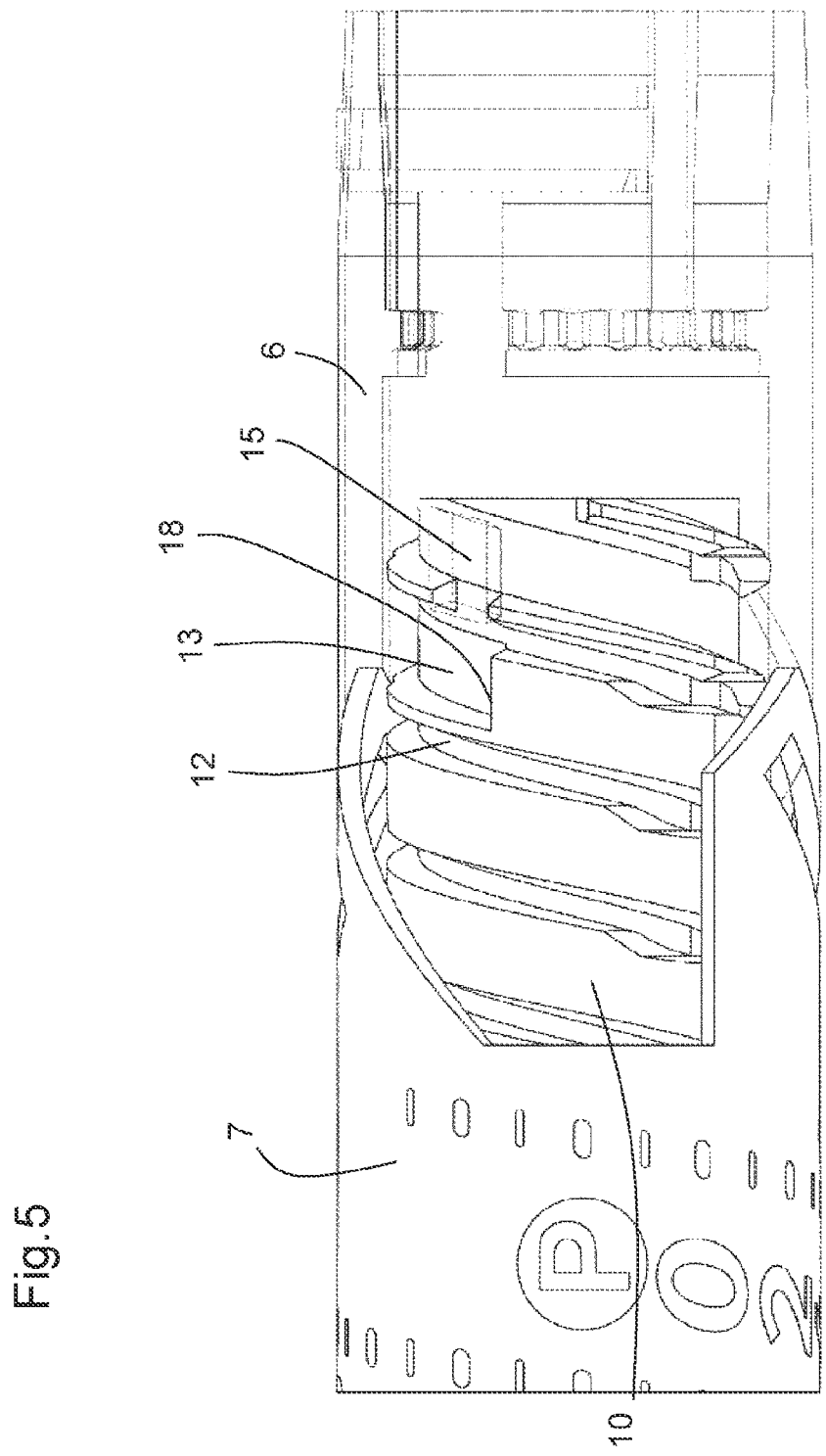
FIG. 5 shows a translucent side view of inner parts of the drug delivery device according to FIG. 1.
Figure 6:
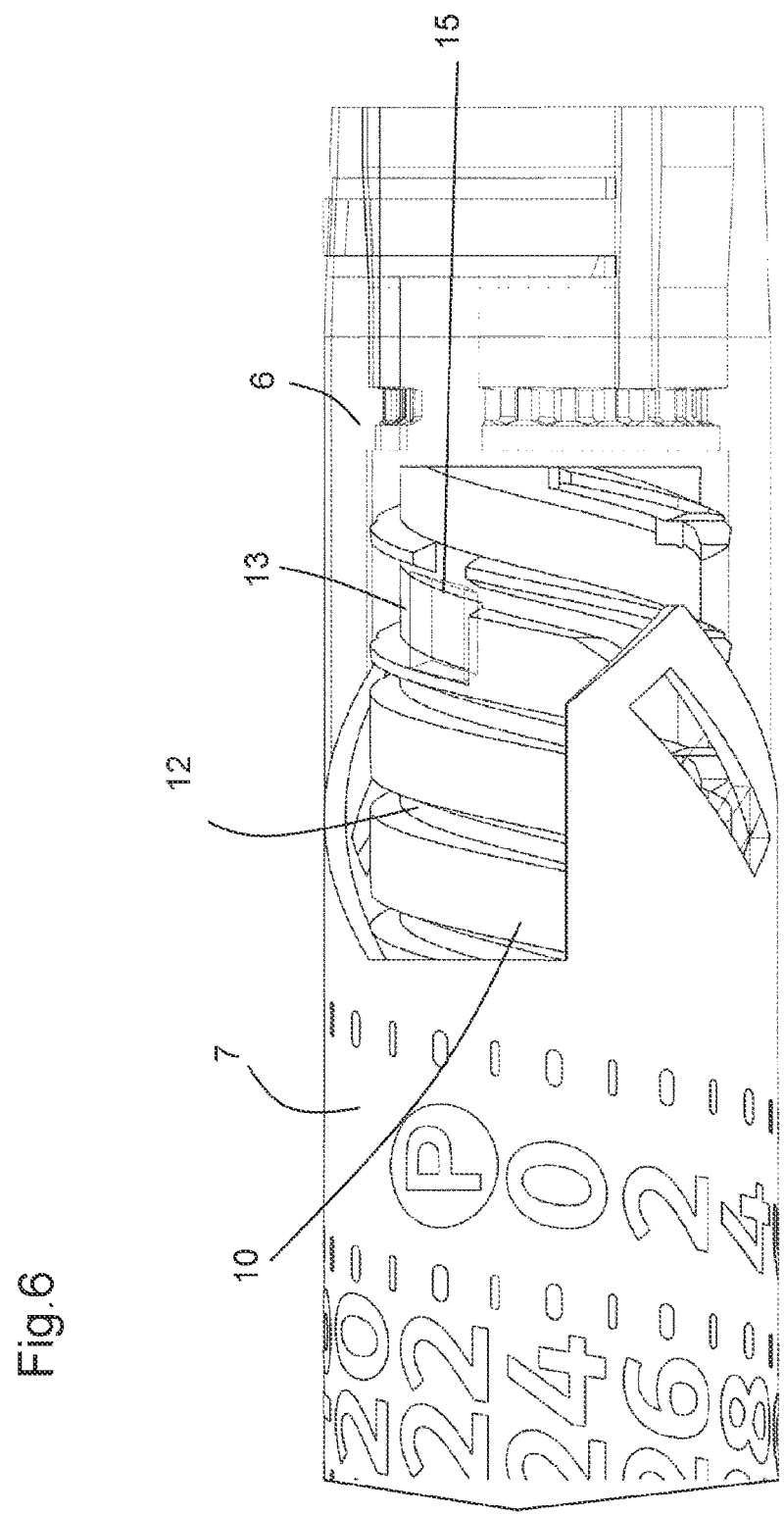
FIG. 6 shows a translucent side view of inner parts of the drug delivery device according to FIG. 2.

FIGS. 5 and 6 represent a translucent view of inner parts of the components according to FIGS. 3 and 4. FIG. 5 represents the initial state according to FIGS. 1 and 3, wherein FIG. 6 represents a primed state according to FIGS. 2 and 4.

According to FIG. 5, the first sleeve member 6 is in its outer position with respect to the second sleeve member 7, wherein the first sleeve member 6 provides a third engagement feature 15 preventing a rotational movement of the first sleeve member 6 with respect to the inner housing 10. In this way, the engagement feature 15 lies in a cutout between two threaded sections of an outer thread 13 of the inner housing 10 and blocks any rotational movement of the first sleeve member 6 with respect to the housing 10. Hence, the first sleeve member 6 can only be axially moved with respect to the inner housing 10 towards a predetermined stop position 18 in order to traverse the assembly from the initial position according to FIGS. 1 and 3 into the primed position according to FIGS. 2 and 4.

FIG. 6 shows the first sleeve member 6 in its second position relative to the second sleeve member 7 according to FIG. 4, wherein the engagement feature 15 now lies in a bay of the threaded section of the outer thread 13 of the inner housing 10. In this position the first sleeve member 6 is enabled to rotate with respect to the inner housing 10 such that the first sleeve member 6 can travel on a helical path in the outer thread 13 with respect to the inner housing 10. In the position according to FIG. 6, corresponding to the position of FIG. 4, first and second sleeve members 6, 7 can together travel on a helical path with respect to the inner housing 10, wherein the first sleeve member 6 travels in the outer thread 13 and the second sleeve member 7 travels in the outer thread 12 of the inner housing 10. Moreover, the defined stop feature 18 (cf. FIG. 5) provides a predetermined position of the first sleeve member 6 relative to the inner housing 10 an delimits the further helical movement of the first sleeve member 6. The stop position according to FIG. 6 can, for example, be an initial dialing position from which any dialing of a predetermined amount of medication can be started. Accordingly, the assembly may return to this discrete position after a dose of a medicament has been delivered to a patient in order to enable subsequent dialing of another dose again starting from this position.

The third engagement feature 15 according to FIGS. 5 and 6 has the advantage that a rotational movement of the first sleeve member 6 together with the button 4 is prevented as long as the assembly has not been securely traversed into the primed state. That means, a user has to perform an axial movement of the button 4 together with the first sleeve member 6 in order to prime the assembly or the drug delivery device 1, respectively, before, for example, a rotational dialing movement of the button 4 together with first and second sleeve members 6, 7 can be performed. Hence, the third engagement feature 15 helps to improve the handling of the device and prevents unintentional or unwilling operation of the device, especially for persons with limited dexterity.

Figure 7:
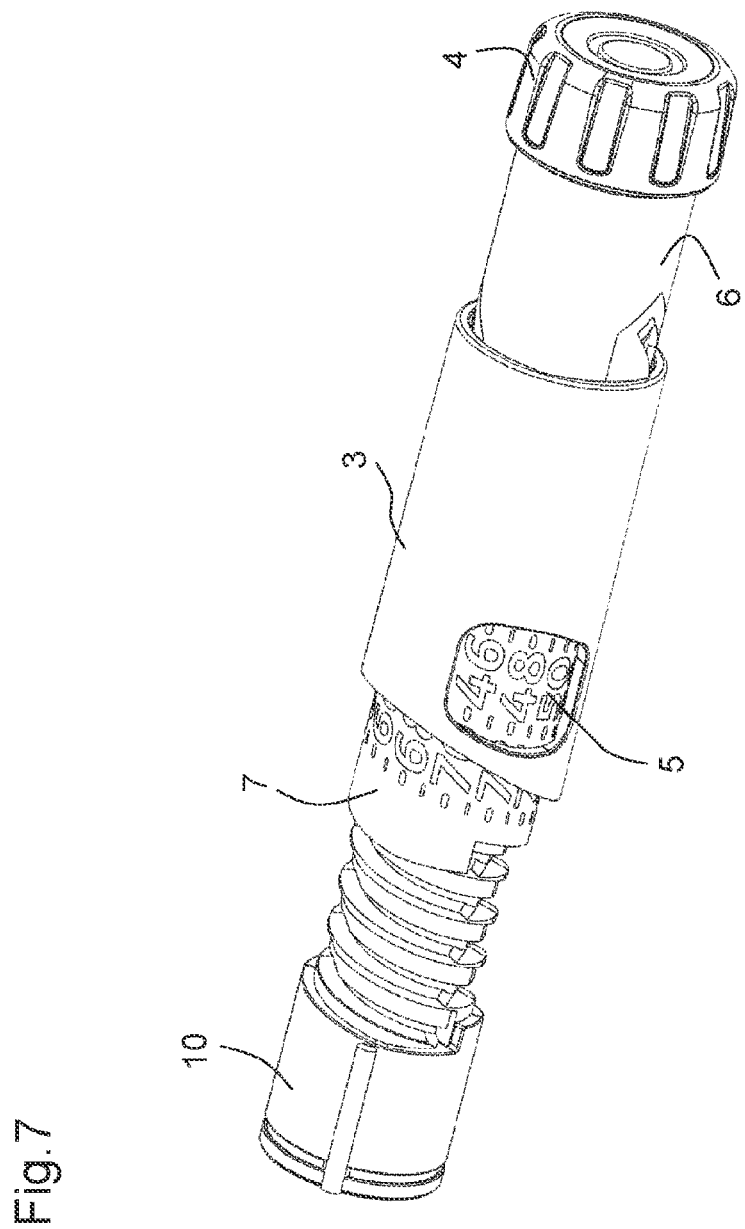
FIG. 7 shows a perspective view of parts of a drug delivery device according to FIGS. 1 and 2 in a third state.

FIG. 7 shows an operational state of components according to FIGS. 3 to 6, after the assembly has been primed. In particular, FIG. 7 shows a dialing state in which a predetermined amount of a medicament, i.e. a predetermined dose, has been dialed. For this purpose, the button 4 and the first sleeve member 6 together with the second sleeve member 7 have been rotated, wherein first and second sleeve members 6, 7 have traveled on a helical path with respect to the inner housing 10 in right direction away from the inner housing 10, such that the button 4 and the first sleeve member 6 project in right direction out of the outer housing 3. Towards the inner housing 10, the outer housing 3 has a cutout and is hidden in order to improve better illustration of the threaded engagement between first and second sleeve members 6, 7 and inner housing 10, without having any influence on the mechanical behavior of the assembly.

During the dialing action, display information 5 is given which indicates a predetermined dose of a medicament. FIG. 7 shows an intermediate stage of dialing (for example 47 of 80 units).

The button 4 together with sleeve members 6, 7 can be moved from the position as depicted in FIG. 7 axially in the left direction towards the inner housing 10 in order to urge a piston rod (not shown) into axial movement with respect to the inner housing 10, such that the dialed dose of a medicament can be expelled out of a cartridge outlet corresponding to a device 1 according to FIGS. 1 and 2.

Figure 8:
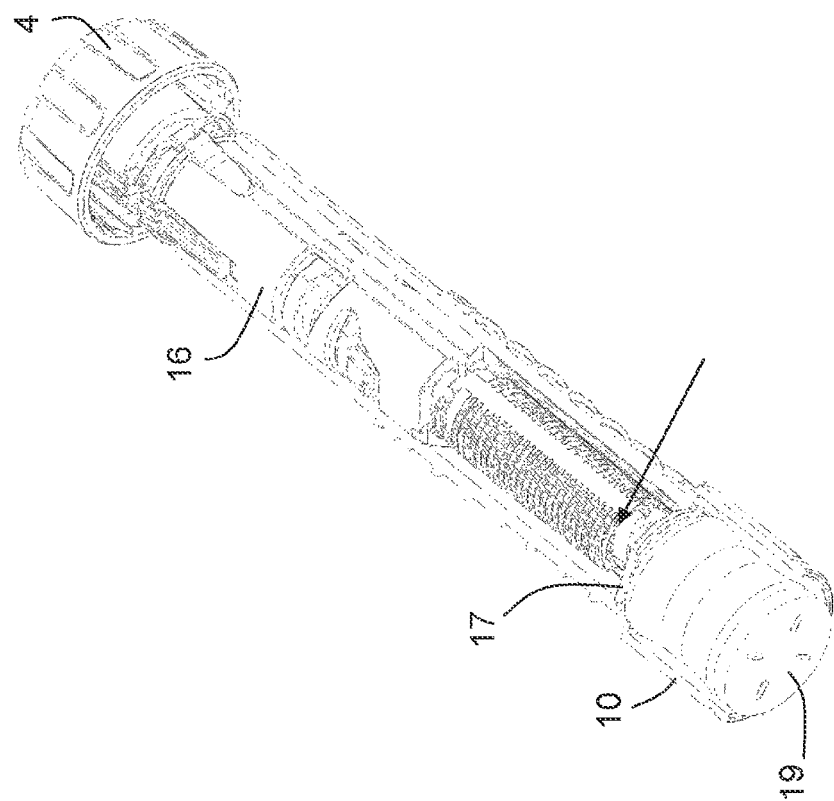
FIG. 8 shows a perspective cut view of parts of a drug delivery device according to FIGS. 1 and 2.

FIG. 8 shows a perspective cut view of the inner housing 10 accommodating a piston rod 17, a driver 16 and at least partly a button 4. The button 4 is coupled to the driver 16, such that a movement of the button 4 is transmitted to the driver 16. In detail, when the button 4 is rotated, the driver 16 is also rotated (for dialing a dose according to FIG. 7, for example); when the button 4 is axially moved with respect to the inner housing 10, the driver 16 also does so.

Additionally, the driver 16 is threadedly coupled with the piston rod 17 (see arrow), such that an axial movement of the driver 16 in the left downward direction urges the piston rod 17 into a helical movement such that the piston rod 17 also is driven into the left downward direction. The piston rod 17 can provide any thread feature for threaded engagement with the driver 16. For example, the piston rod 16 can provided a twin thread arrangement.

In particular, FIG. 8 depicts a transition from an initial position of the piston rod 17 into a primed position of the piston rod 17, in which position the piston rod 17 abuts a bung 19 of a cartridge 2 according to FIGS. 1 and 2. In this way, an intentional gap between the piston rod 17 in its initial position and a bung 19 of a cartridge 2 can be removed. This can be done by moving the button 4 together with the first sleeve member 6 according to the explanations in the context of FIGS. 3 and 4.

Upon transition of the piston rod 17 into its primed position (see position of piston rod 17 as depicted in FIG. 8), the assembly can be used to dial and dispense predetermined doses of a medicament, wherein dialing takes place according to the explanations in the context of FIG. 7, and wherein dispensing takes place according to the explanations in the context of FIG. 8. The latter operation takes place by axially pressing the button 4 and the driver 16 in the direction of the bung 19 in the inner housing 10, such that the piston rod 17 is also driven in axial direction and pushes the bung 19 such that medication can be expelled out of a cartridge 2 of the device 1 according to FIGS. 1 and 2.

The described embodiments are only exemplary embodiments without restricting the basic idea of the disclosure, wherein a transition of an assembly for a drug delivery device from an initial state into a primed state may be performed, with the first and second sleeve members 6, 7 being movable to each other in the initial state and being permanently rotationally and axially locked to each other in a primed state. This enables a piston rod to be traversed from an initial position to a predetermined second position in which the piston rod is in a primed state. In this way, an air gap between the piston rod and a cartridge bung in an initial state of the assembly can be removed. This helps for better handling and preparing a drug delivery device for further operation, without the need of performing "air shots" and discarding expensive medication for priming the drug delivery device.

The invention claimed is:

1. Assembly for a drug delivery device comprising a housing part, a piston rod displaceable relative to the housing part, a first sleeve member and a second sleeve member, first and second sleeve members being coupled to the housing part, wherein in an initial state of the assembly the first sleeve member is movable from an initial position to a second position relative to the second sleeve member, wherein movement of the first sleeve member relative to the second sleeve member in the initial state of the assembly is related to an axial travel of the piston rod from an initial position to a predetermined second position which allows the piston rod to axially travel from its initial position to its predetermined second position such that the assembly is in a primed state, wherein the first sleeve member engages with the housing part via a third engagement feature such that between the initial position and the second position of the first sleeve member relative to the second sleeve member a rotational movement of the first sleeve member relative to the housing part is prevented, wherein in the primed state of the assembly, with the first sleeve member being in the second position relative to the second sleeve member, first and second sleeve members are permanently rotationally and axially locked to each other by a first engagement feature such that first and second sleeve members together form a sleeve, and wherein once the assembly has been traversed from its initial state to its primed state, the assembly remains in the primed state during further operation of the assembly.

2. The assembly according to claim 1, comprising a driver coupled to the piston rod for driving the piston rod.

3. The assembly according to claim 2, comprising a button arranged at a proximal end of the assembly and coupled to the first sleeve member and to the driver.

4. The assembly according to claim 3, wherein in the initial state of the assembly the button is enabled to axially travel relative to the second sleeve member, the button during its axial travel entraining the driver such that the driver is axially displaced relative to the housing part, thereby urging the piston rod into its axial movement from the initial position to the predetermined second position.

5. The assembly according to claim 3, wherein in the second position of the first sleeve member relative to the second sleeve member for dose setting the button is rotatable which entrains the driver and first and second sleeve members such that the button, the driver and first and second sleeve members are moved on a helical path relative to the housing part and the piston rod, and for dose dispensing the button is axially displaceable which entrains the driver and first and second sleeve members such that the button, the driver and first and second sleeve members are axially moved relative to the housing part and the piston rod, with first and second sleeve members and the piston rod rotating relative to the housing part, the button and the driver.

6. The assembly according to claim 1, wherein the first sleeve member engages with the second sleeve member via a second engagement feature such that in the initial position of the first sleeve member a maximum clearance between respective walls of first and second sleeve members is limited to a predetermined clearance.

7. The assembly according to claim 1, wherein the movement of the first sleeve member from its initial position to its second position relative to the second sleeve member is non-reversible.

8. The assembly according to claim 1, wherein the housing part comprises a first outer thread and wherein in the second position of the first sleeve member relative to the second sleeve member the third engagement feature engages with the first outer thread of the housing part such that the first sleeve member is movable on a helical path relative to the housing part.

9. The assembly according to claim 8, wherein the first outer thread of the housing part is designed such that it delimits a predetermined stop position of the third engagement feature relative to the housing part.

10. The assembly according to claim 1, wherein the second sleeve member comprises an inner thread engaging a second outer thread of the housing part such that the second sleeve member is movable on a helical path relative to the housing part.

11. The assembly according to claim 10, wherein first and second sleeve members are in threaded engagement with each other, and wherein the movement of the first sleeve member from its initial position to its second position relative to the second sleeve member urges the second sleeve member into a rotational movement relative to the housing part and to the first sleeve member such that the second sleeve member moves on the helical path relative to the housing part in a direction opposite to the direction of movement of the first sleeve member.

12. The assembly according to claim 11, wherein during movement of the second sleeve member on the helical path relative to the housing part a display information provided by the second sleeve member is designed to change from an initial state information to a primed state information.

13. The assembly according to claim 1, wherein the second sleeve member provides dosing indicia for setting a predetermined dose of a medicament.

14. A drug delivery device for selecting and dispensing a number of doses of a medicament, comprising a housing, a cartridge containing the medicament and an assembly according to claim 1.

* * * * *